US008962032B2

(12) United States Patent
Scott et al.

(10) Patent No.: US 8,962,032 B2

(45) Date of Patent: Feb. 24, 2015

(54) MODULATOR

(75) Inventors: Christopher Scott, Belfast (GB); James Johnston, Belfast (GB); Shaun Spence, Belfast (GB); Danny McAuley, Belfast (GB); Francois Fay, Belfast (GB)

(73) Assignee: The Queen's University of Belfast, Belfast (GB)

(*) Notice: Subject to any disclaimer, the term of this patent is extended or adjusted under 35 U.S.C. 154(b) by 0 days.

(21) Appl. No.: 13/515,884

(22) PCT Filed: Dec. 17, 2010

(86) PCT No.: PCT/GB2010/052145

§ 371 (c)(1), (2), (4) Date: Jul. 31, 2012

(87) PCT Pub. No.: WO2011/073685

PCT Pub. Date: Jun. 23, 2011

(65) Prior Publication Data

US 2012/0294946 A1 Nov. 22, 2012

(30) Foreign Application Priority Data

Dec. 17, 2009 (GB) ................................ 09220666.6

(51) Int. Cl.

*A61P 11/00* (2006.01)
*A61P 31/06* (2006.01)
*A61P 11/06* (2006.01)
*A61P 11/08* (2006.01)
*A61P 31/00* (2006.01)
*A61P 9/00* (2006.01)
*A61P 37/00* (2006.01)
*A61P 3/10* (2006.01)
*A61P 25/00* (2006.01)
*A61K 9/14* (2006.01)
*A61K 31/702* (2006.01)
*A61K 47/48* (2006.01)
*A61K 45/06* (2006.01)

(52) U.S. Cl.

CPC ........... *A61K 47/48853* (2013.01); *A61K 45/06* (2013.01); *A61K 47/482* (2013.01); *A61K 47/4823* (2013.01); *A61K 47/48915* (2013.01); *A61K 47/48923* (2013.01); *Y10S 977/773* (2013.01); *Y10S 977/906* (2013.01)

USPC ............. 424/493; 514/61; 977/773; 977/906

(58) Field of Classification Search

None

See application file for complete search history.

(56) References Cited

U.S. PATENT DOCUMENTS

| | | | |
|---|---|---|---|
| 5,846,951 A | 12/1998 | Gregoriadis | |
| 6,235,313 B1 | 5/2001 | Mathiowitz et al. | |
| 6,528,097 B1 | 3/2003 | Vaughn et al. | |
| 6,616,946 B1 | 9/2003 | Meier et al. | |
| 7,731,967 B2 | 6/2010 | O'Hagan et al. | |
| 2001/0007760 A1* | 7/2001 | Palcic et al. | 435/97 |
| 2005/0266067 A1 | 12/2005 | Sengupta et al. | |
| 2006/0002852 A1 | 1/2006 | Saltzman et al. | |
| 2007/0244038 A1* | 10/2007 | Varki et al. | 514/8 |
| 2008/0220988 A1 | 9/2008 | Zhou | |
| 2008/0269875 A1 | 10/2008 | Zhao | |
| 2008/0286372 A1 | 11/2008 | Pacetti et al. | |
| 2009/0047272 A1 | 2/2009 | Appelbaum et al. | |
| 2009/0087494 A1 | 4/2009 | Kompella et al. | |
| 2009/0169636 A1 | 7/2009 | O'Hagan et al. | |
| 2009/0298710 A1 | 12/2009 | Farokhzad et al. | |
| 2010/0190257 A1 | 7/2010 | Salem et al. | |
| 2011/0052715 A1 | 3/2011 | Davis et al. | |

FOREIGN PATENT DOCUMENTS

| | | | |
|---|---|---|---|
| CN | 1903365 | A | 1/2007 |
| CN | 101711740 | A | 5/2010 |
| EP | 2070521 | A1 | 6/2009 |
| WO | WO-95/20959 | A1 | 8/1995 |
| WO | WO-2005/084710 | A2 | 9/2005 |
| WO | WO-2010008792 | A1 | 1/2010 |
| WO | WO-2011071970 | A2 | 6/2011 |

OTHER PUBLICATIONS

Gupta et al., "Targeting cells for drug and gene delivery: Emerging applications of mannans and mannan binding lectins", Jun. 2009, Journal of Scientific and Industrial Research, vol. 68, pp. 465-483.*

Blixt, Ola, et al., "Sialoside Specificity of the Siglec Family Assessed Using Novel Multivalent Probes", The Journal of Biological Chemistry, vol. 278, No. 33, Aug. 15, 2003, pp. 31007-31019.

Offermann, Stefanie, "International Search Report" for PCT/GB2010/052145 as mailed May 20, 2011, 4 pages.

Jayant, Sreeja, et al, "Targeted Sialic Acid-Doxorubicin Prodrugs for Intracellular Delivery and Cancer Treatment", Pharmaceutical Research, vol. 24, No. 11, Aug. 1, 2007, pp. 2120-2130.

Cheng, Jianjun, et al, "Formulation of Functionalized PLGA-PEG Nanoparticles for In Vivo Targeted Drug Delivery", Biomaterials, vol. 28, No. 5, Nov. 6, 2006, pp. 869-876.

Boyd, Caroline R., et al, "Siglec-E is Up-Regulated and Phosphorylated Following Lipopolysaccharide Stimulation in Order to Limit TLR-Driven Cytokine Production", Journal of Immunology, vol. 183, No. 12, Nov. 23, 2009, pp. 7703-7709.

(Continued)

*Primary Examiner* — Robert A Wax

*Assistant Examiner* — Randeep Singh

(74) *Attorney, Agent, or Firm* — Winstead PC

(57) ABSTRACT

There is provided a method for suppressing a pro-inflammatory immune response in a cell, comprising providing to a cell sialic acid or analogs thereof, wherein the sialic acid or analogs are presented by a substrate such that a pro-inflammatory immune response in a cell is suppressed or an anti-inflammatory immune response is increased in a cell. Further, there is provided a method of treatment of inflammatory disease in a subject in need thereof. There is also provided a drug delivery device and a biomaterial which can modulate the inflammatory response in a subject.

17 Claims, 16 Drawing Sheets

(56) References Cited

OTHER PUBLICATIONS

Figure 1:
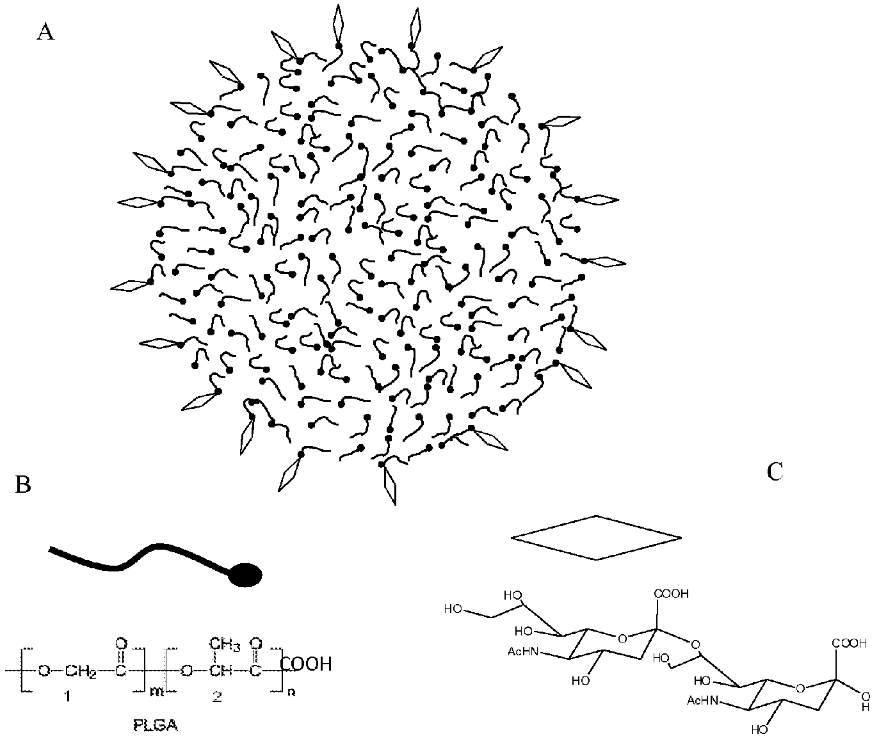

Tosi, G., et al, "Sialic Acid and Glycopeptides Conjugated PLGA Nanoparticles for Central Nervous System Targeting: In Vivo Pharmacological Evidence and Biodistribution", Journal of Controlled Release, vol. 145, No. 1, Jul. 1, 2010, pp. 49-57.
Bondioli, Lucia, et al, "PLGA Nanoparticles Surface Decorated with the Sialic Acid, N-Acetylneuraminic Acid", Biomaterials, vol. 31, No. 12, Apr. 2010, pp. 3395-3403.
Oka et al., Syntheses and biological evaluations of carbosilane dendrimers uniformly functionalized with sialyl α(2→3) lactose moities as inhibitors for human influenza viruses, Bioorganic & Medicinal Chemistry, vol. 17, 5465-5475 (2009).
Ho et al., Sialic Acid reduces Acture Endotoxemia-Induced Liver Dysfunction in the Rat, Shock, vol. 32 (2), 228-235 (2009).
Julkunen et al., Inflammatory Responses in influenza A virus infection, Vaccine, vol. 19, 832-837 (2001).

* cited by examiner

| Conjugation efficiency | Quantity of alpha 2-8 di Acetylneuraminic acids conjugated to 1mg of PLGA |
|---|---|
| 15% | 15μg ± 8 |

Figure 2

(A)

| | NP non conjugated | NP conjugated with alpha 2-8 di Acetylneuraminic acids |
|---|---|---|
| size | 151 nm ± 10 | 152 nm ± 13 |
| zeta potential | 0.4 mv ± 0.4 | 0.3mv ± 0.2 |

(B)

MODULATOR

FIELD OF INVENTION

The present invention relates to inflammation, inflammatory disease, pulmonary disease and blood cancers, in particular to a device for the treatment of inflammatory conditions and leukaemia, specifically Acute Myeloid Leukaemia (AML). It further relates to a drug delivery method and a device for the delivery of drugs to particular cell types.

BACKGROUND OF THE INVENTION

Aberrant mediation of the inflammatory response by cells is known to lead to disease in a number of cell or tissue types, for example, inflammatory conditions of the lung, including Tuberculosis, Chronic Obstructive Pulmonary Disorder (COPD), asthma, and acute lung injury, rheumatoid arthritis, Crohn's disease, ulcerative colitis, SLE, and acute and chronic skin diseases including dermatitis.

Therefore there is a need to identify agents which can be used for the treatment of inflammation, particularly for inhibiting an inflammatory response in cells.

SUMMARY OF THE INVENTION

The inventors have determined a method to suitably provide sialic acid or analogs thereof, capable of targeting cells comprising sialic-acid-binding immunoglobulin-like lectin (siglec) receptors, such that binding of the sialic acids to the targeted cells promotes a reduction in an inflammatory response in the targeted cells and associated environment.

Further, such sialic acid bound microparticles or nanoparticles can be used to deliver drugs to the blood and lymphoma-type tumours as it is known that cell types including sialic-acid-binding immunoglobulin-like lectin (siglec) receptors are associated with blood cancer, and in particular with leukaemia and lymphomas which account for 6 to 8% of the total cancer diagnoses worldwide.

Accordingly, the present invention provides a method of modulating an inflammatory response in a cell, the method comprising:

providing sialic acid or analogs thereof to a cell, wherein the sialic acid or analogs are presented on a substrate such that a pro-inflammatory response in a cell is suppressed or an anti-inflammatory response in increased in a cell.

In embodiments the method provides for the suppression of a pro-inflammatory response. In alternative embodiments the method provides for the increase in an anti-inflammatory response. In embodiments the pro-inflammatory response can be suppressed by at least 10%, at least 20%, at least 30%, at least 40%, at least 50%. In alternative embodiments the anti-inflammatory response can be increased by at least 10%, at least 20%, at least 30%, at least 40%, at least 50%. In yet further embodiments there can be provided the suppression of a pro-inflammatory response and an increase in an anti-inflammatory response. Suitably pro-inflammatory cytokines can be measured, for example TNF alpha. In embodiments, pro-inflammatory cytokines can include TNF alpha and IL-6. Suitably anti-inflammatory cytokines can be measured, for example IL-10. The skilled person would know of suitable assay methods to measure such cytokines, for example the Bio-Plex™ Cytokine Assay (Bio-Rad). To determine whether a cell produces greater or less proinflammatory cytokines, a suitable method which can be used is that cells are resuspended and seeded at $2\times10^5$ cells/ml and 200 μl per well in a 96 well plate. They can then be left to adhere to the plate overnight and be treated with LPS and ligands for 24 hours at range of concentrations. Supernatant can then be removed and stored at −70° C. Cytokine levels can then be assessed by ELISA (R&D systems). As will be appreciated a similar method can be applied to determine anti-inflammatory cytokines.

In an embodiment, TNF-α levels can be suitably determined by coating a 96 well plate with TNF-α capture antibody diluted in 1× phosphate buffered saline (PBS) overnight. All steps can be carried out at room temperature. The wells can be washed three times in 1×PBS/0.1% Polyoxyethylene sorbitan monolaurate (Tween 20) before being blocked for one hour with 1% BSA (BDH) dissolved in 1×PBS. The washing step can be repeated and 50 μl of treated cell supernatants or standards ranging from 2000 pg/ml to 0 pg/ml can be added to the wells and left for 2 hours. Subsequently supernatant can be aspirated out, the wells washed 3 times and 50 μl of TNF-α detection antibody diluted in 1% BSA/1×PBS can be added for 2 hours. Again wells can be washed three times and Horse Radish Peroxidase (HRP) conjugated antibody can be added at 1 in 200 dilution in 1% BSA/1×PBS for 20 minutes. At this stage the plate can be covered in aluminium foil. Once wells have been washed 3,3',5,5'-tetramethylbenzidine (TMB) can be added for 20 minutes and again protected from light. 1M hydrochloric acid can be added to halt the reaction and absorbance read on a plate reader at 450 nM. TNF-α concentrations can then be extrapolated from the standard curve. As will be appreciated, a similar methodology can be applied to determine other cytokines.

In an embodiment, IL-10 levels can be suitably determined by coating a 96 well plate with IL-10 capture antibody diluted in 1× phosphate buffered saline (PBS) overnight. All steps can be carried out at room temperature. The wells can be washed three times in 1×PBS/0.1% Polyoxyethylene sorbitan monolaurate (Tween 20) before being blocked for one hour with 1% BSA (BDH) dissolved in 1×PBS. The washing step can be repeated and 50 μl of treated cell supernatants or standards ranging from 2000 pg/ml to 0 pg/ml can be added to the wells and left for 2 hours. Subsequently supernatant can be aspirated out, the wells washed 3 times and 50 μl of IL-10 detection antibody diluted in 1% BSA/1×PBS can be added for 2 hours. Again wells can be washed three times and Horse Radish Peroxidase (HRP) conjugated antibody can be added at 1 in 200 dilution in 1% BSA/1×PBS for 20 minutes. At this stage the plate can be covered in aluminium foil. Once wells have been washed 3,3',5,5'-tetramethylbenzidine (TMB) can be added for 20 minutes and again protected from light. 1M hydrochloric acid can be added to halt the reaction and absorbance read on a plate reader at 450 nM. IL-10 concentrations can then be extrapolated from the standard curve. As will be appreciated, a similar methodology can be applied to determine other cytokines.

To determine in vivo whether the animal produces a greater or lesser pro-inflammatory response, a suitable method which can be used is analysis of serum cytokine levels. For example this may be achieved by the collection of 50 μl blood from the tail vein of the animal using a capillary tube. This blood is allowed to clot at room temperature for 30 minutes prior to centrifugation at 1300 rpm to pellet red blood cells. Serum is decanted to a clean micro-centrifuge tube and analysed by ELISA. For more extensive analysis, a larger volume of blood (approximately 600 μl–1 ml) may be taken by direct cardiac puncture, thus allowing for a greater volume of serum to be collected and analysed by ELISA or such other technique. Other suitable techniques will be known in the art, particularly to detect and measure cytokines in humans.

The substrate can be coated with or conjoined to sialic acid or a sialic acid analog. Sialic acid analogs are known in the art. In embodiments such analogs can have substitutes at position C9. Analogs can include neuraminic acid derivates, sialosides, and any sugars comprising at least one neuraminic acid molecule. Suitably, the sialic acid or an analog thereof may be immobilised on the surface of the substrate. The sialic acid may be bound directly to the substrate or via a linker. The substrate may be derivatised or activated to allow binding of the sialic acid or analog. Alternatively, the substrate may be derivatised or activated to allow binding of a linker to a substrate and the linker may be attached to sialic acid. By coating or conjoining sialic acid or an analog thereof to a substrate, a device including said substrate can be adapted to target a cell comprising a siglec receptor to induce binding of the siglec receptor such that production of pro-inflammatory cytokines within the cell is inhibited or production of anti-inflammatory cytokines is increased, thereby suppressing a pro-inflammatory immune response. The substrate can be provided to a device to provide the device with sialic acid on non-surface. In embodiments wherein a coating is provided to a device, the coating can be resistant to washing. In embodiments the conjoining or coating of sialic acids to a substrate, for example a drug delivery device, can be by covalent bonds. In alternative embodiments the sialic acid can be bound to the substrate by strong non-covalent bonds, for example via a streptavidin-biotin linkage. Suitably, a biotin molecule can be attached to the sialic acid via a linker to create a probe which can be conjoined to a device via a streptavidin linker (see for example Blixt et al., Journal of Biological Chemistry, 278, 33, 31007-31019). Techniques as known in the art to conjoin or coat sialic acid to polymers or different substrate materials could be utilised as required. For example, a substrate surface can be surfaced-functionalised to allow binding and immobilisation of the sialic acid or an analog thereof thereon.

In embodiments, the substrate can be a drug delivery device. In embodiments the substrate can be a biomaterial, for example an implantable medical device, for example a prosthetic implant, support or the like. An implantable medical device can be formed of plastics material, metal or another biocompatible and/or biostable material as known in the art. In further embodiments the substrate can be a quantum dot or the like.

By presented on a substrate is meant the sialic acid or analogs thereof are provided on the substrate such that they are available to be bound by a siglec receptor on a cell. Suitably they may be provided to both bind and activate the receptor. Without wishing to be bound by theory the presentation on the sialic acid on a substrate is believed to cause the sialic acid to be provided at a concentration density such that the inflammatory response is modulated.

The substrate provides a surface for presentation or display of the sialic acid or an analog thereof. The substrate thus acts as a scaffold to arrange the sialic acid or an analog thereof on the surface of a device, for example a nanoparticle or microparticle or a biomaterial, which can be further used to deliver a therapeutic to a cell. The substrate may provide a multivalent complex of the sialic acid which enables binding to siglec receptors to provide for the modulation of the inflammatory response. In embodiments, the presentation of sialic acid or an analog thereof on the substrate of a nanoparticle can provide for an increased uptake of the nanoparticle by a cell of at least two-fold, at least three-fold, at least four fold, at least five fold, at least six fold, or at least 10 fold.

In embodiments, the sialic acid or analogs thereof can be presented on the substrate in groups of at least 2, at least 5, at least 10, at least 15, at least 20 or at least 25, at least 50, at least 100, at least 200, at least 400. In embodiments the sialic acid or analogs thereof can be spaced on the surface of the substrate such that they or the substrate can bind to more than one siglec receptor. In embodiments, the sialic acid or analogs thereof can be spaced on the surface of the substrate such that they or the substrate can bind to multiple siglec receptors presented on individual cell types, which may vary in the quantity of siglec receptors presented on their plasma membrane.

In such embodiments, the substrate can be a drug delivery device or can be applied to a drug delivery device.

In embodiments a drug delivery device can be a microparticle with a greatest cross-sectional width less than 1000 micrometers and which is greater than or equal to 1 micrometer. Such a microparticle may be particularly effective for use in the treatment of diseases of the lung.

In alternative embodiments, a drug delivery device can be a nanoparticle. Suitably, in embodiments binding of the sialic acid or sialic acid analog presented on a nanoparticle to a siglec receptor of a cell can induce binding of the siglec receptor and internalisation of the nanoparticle. Where a drug is provided by the nanoparticle, the drug of the nanoparticle can then be specifically delivered to the cell into the cell.

In embodiments a nanoparticle of the invention can have a greatest cross-sectional width or diameter of less than 1000 nm, less than 500 nm, less than 250 nm or less than 200 nm. In embodiments a nanoparticle can have a width greater than 1 nm, greater than 10 nm, greater than 50 nm, or greater than 100 nm. In embodiments, a nanoparticle coated with sialic acid or a sialic acid analog can have a greatest cross-sectional width or diameter in the range of 130 nm to 170 nm, more preferably a width of around 150 nm. In embodiments these range of sizes can be average widths of nanoparticles. In embodiments at least 80% of the nanoparticles live within a disclosed range.

Suitably, in embodiments around at least 80%, more preferably at least 90% of the particles have a greatest cross-sectional width between 130 nm to 170 nm. In embodiments the particles can have an average greatest cross-sectional width of 150 nm with the particles having no width greater or less than a value not within one standard deviation of 150 nm. In embodiments, a nanoparticle can have a volume equal to that of a sphere with a diameter between 10 nm to 500 nm, suitably between 50 nm to 250 nm, or 100 nm to 200 nm, or 130 nm to 170 nm.

In embodiments of the method wherein the substrate is provided by a nanoparticle, the inventors have determined that binding to a siglec receptor on a cell can inhibit production of pro-inflammatory cytokines by the cell and induce anti-inflammatory cytokines. In embodiments binding to the siglec receptor can induce internalisation of the nanoparticle into the cell. In embodiments wherein the substrate is provided by a nanoparticle, the binding of a nanoparticle to a siglec receptor on a cell can result in activation of the receptor and can induce internalisation of the receptor and the nanoparticle into the cell. Production of pro-inflammatory cytokines by the cell has been observed to be inhibited and/or the production of anti-inflammatory cytokines has been observed to be increased following internalisation of a nanoparticle as discussed herein thereby suppressing a pro-inflammatory immune response.

As will be appreciated, in embodiments a nanoparticle or microparticle can also include an active agent which can be specifically delivered to a cell which expresses a siglec receptor, for example to cells associated with leukaemia and lymphomas.

In embodiments a nanoparticle for use in the treatment of lymphoma can be loaded with doxorubicin. In embodiments such nanoparticles can include a substrate comprising sialic acid which has binding specificity and affinity to B-cell specific members of the sialic acid binding Ig-like lectin (siglec) family, for example α2-6-linked sialic acid, in particular a trisaccharide sialic acid based on NeuAcα2-6Galβ1-4GlcNAc, more particularly 9-N-biphenylcarboxyl-NeuAcα2-6Galβ1-4GlcNAc ($^{BPC}$NeuAc).

In embodiments, the presentation of sialic acid or analogs by a substrate can allow nanoparticle comprising the substrate to be internalised by a cell.

Suitably, nanoparticle internalisation by a cell following binding and/or activation of a siglec receptor may be visualised by confocal microscopy. For example, in a method to determine nanoparticle internalisation, RAW 264.7 cells may be cultured in DMEM medium containing 1-glutamine, penicillin/streptomycin and 10% v/v foetal calf serum. In such a method, cells can be seeded on cover slips in six-well plates at $2.5\times10^5$ cells per well and allowed to grow overnight. This can be followed by 3 hours of incubation at 37 degrees C. and 5% $CO_2$ in serum free media with 100.0 μl dispersion of 100 μg $ml^{-1}$ dye-loaded nanoparticle conjugated with sialic acid or non conjugated nanoparticles suspended in PBS. Cells can be washed three times with PBS then fixed in 4% paraformaldehyde (PFA) for 1 hour, and washed three times with ice-cold PBS for 30 min in pH 8 HEPES buffer. For nucleus staining, cells can be incubated with 1/200 solution of TO-PRO®-3 iodide (Invitrogen) solution and subsequently washed 3 times with PBS. Cover-slips can then be mounted on microscope slides using Slow Fade® Gold reagent (Invitrogen) and sample analysis performed using confocal scanning laser microscopy (Leica Confocal TCS Sp2, Germany). Excitation can be done using laser illumination at 488 nm for green fluorescence 543 nm for red fluorescence and 633 nm for far red fluorescence. Internalisation of the nanoparticles can then be assessed by considering the patterns of fluorescence.

The inventors consider that any suitable sialic acids can be used in the invention. By the term sialic acid is any monosialic acid or polysialic acid, including disialic acids which can bind to a siglec receptor, in particular a sialic acid with binding specificity to inhibitory siglec receptors, such as siglec 7. In embodiments a sialic acid for use in the present invention can be any group of amino carbohydrates that are components of mucoproteins and glycoproteins in animal tissue and blood cells. In embodiments sialic acids (also known as nonulosonic acids) are members of a family of amino containing sugars containing 9 or more carbon atoms, for example N-acetylneuraminic acid (also known as 5-(acetylamino)-3, 5-dideoxy-D-glycero-D-D-galacto-nonulosonic, lactaminic acid and O-sialic acid).

In embodiments, the inventors envisage the sialic acids can be monosialic acids, or polysialic acids, including disialic acids.

Polysialic acids may be linked 2→8 and/or 2→9, and/or 2→6, and/or 2→3, usually in the α-configuration.

In embodiments wherein the sialic acids conjoined or coated onto the substrate, for example a drug delivery device, are polysialic acid, they may be less than 5 sialic acid units, preferably less than 4 sialic acid units, less than 3 sialic acid units long, most preferably, 2 sialic acid units in length.

In alternative embodiments the sialic acids or analogs thereof which are conjoined or coated onto the substrate can be monosialic acids.

In embodiments wherein an analog of sialic acid is used, the analog may be a structural mimetic of a sialic acid as disclosed herein which can bind to certain siglecs, but lack the sialic acid of the natural siglec ligand. Suitable analogs would be known in the art. It is believed that the feature which influences binding of the sialic acid ligand to a siglec receptor is the charge-distance-coordination relationship between the carboxylic acid functionality of sialic acid.

In embodiments of the present invention the substrate, for example of a device such as a microparticle or a nanoparticle or as coated on a device, can be provided with sialic acid selected from
NeuAcα2-3Galβ1-4Glc,
NeuAcα2-3Galβ1-4GlcNAc,
NeuAcα2-3Galβ1-3GlcNAc,
NeuAcα2-3Galβ1-3GalNAc,
NeuGcα2-3Galβ1-4GlcNAc,
NeuGcα2-3Galβ1-3GlcNAc,
NeuAcα2-6Galβ1-4Glc,
NeuAcα2-6Galβ1-4GlcNAc,
NeuAcα2-6GalNAc,
Galβ1-3(NeuAcα2-6)GalNAc,
NeuGcα2-6Galβ1-4Glc,
NeuGcα2-6Galβ1-4GlcNAc,
NeuGcα2-6GalNAc,
NeuAcα2-8NeuAcα2-3Galβ1-4Glc,
NeuAcα2-6Galβ1-4GlcNAc,
NeuAcα2-3Galβ1-4[Fucα1-3]GlcNAc,
NeuAcα2-6Galβ1-4GlcNAc6S,
NeuAcα2-3Galβ1-4GalNAc,
NeuAcα2-8NeuAc,
NeuAcα2-3GalβSβ1-4GlcNAcα2-3Fuc,
NeuAcα2-3Galβ1-4GlcNAc6Sα2-3Fuc, and
NeuAcα2-8NeuAc or sialoside derivatives of such sialic acids, for example $^{BPC}$NeuAc sialosides.

In embodiments, a sialic acid for use in the invention can be selected according to the siglec receptor being targeted wherein the binding preference for particular siglecs may be selected from Table 1.

TABLE 1

| | |
|---|---|
| siglec 1 | NeuAcα2-3Galβ1-4GlcNAc |
| siglec 2 | NeuAcα2-6Galβ1-4GlcNAc6S |
| siglec 3 | NeuAcα2-6Galβ1-4GlcNAc |
| siglec 4 | NeuAcα2-3Galβ1-4GalNAc |
| siglec 5 | NeuAcα2-8NeuAc |
| siglec 6 | NeuAcα2-8NeuAc |
| siglec 7 | NeuAcα2-8NeuAcα2-3Galβ1-4Glc |
| siglec 8 | NeuAcα2-3Gal6Sβ1-4GlcNAcα2-3Fuc |
| siglec 9 | NeuAcα2-3Galβ1-4GlcNAc6Sα2-3Fuc |
| siglec 10 | NeuAcα2-6Galβ1-4GlcNAc |
| siglec 11 | NeuAcα2-8NeuAc |
| siglec 14 | NeuAcα2-8NeuAc |
| siglec 15 | NeuAcα2-6GalNAc |
| siglec 16 | NeuAcα2-8NeuAc |

In embodiments, appropriate sialic acid ligands or analogs can be provided to the substrate, for example a drug delivery device, according to the specificity desired.

Preferably the sialic acid of the substrate, is at least one of 2-8 disialic acid, or 2-6 or 2-3 variants with at least one position filled with a sialic acid. More preferably the sialic acid can be selected from at least one of alpha 2-8 di-acetylneuraminic acid, alpha-NeuNAc-(2→6)-β-D-Gal-(1→4)-D-Glc and alpha-NeuNAc-(2→3)-β-D-Gal-(1→4)-D-Glc. In particular embodiments the substrate can be provided with alpha 2-8 acetylneuraminic acid.

In embodiments the substrate can form a coated device or biomaterial, for example a microparticle or nanoparticle or medical device.

In alternative embodiments the substrate can form the device, for example a microparticle or a nanoparticle, for example the nanoparticle is formed entirely by the substrate. In such embodiments a polymer with the sialic acid bound thereto can form the device, for example a polymer such as PGLA can form the drug delivery device, for example a nanoparticle.

Any suitable material as known in the art to form a microparticle or nanoparticle may be suitably utilised. For example gold, polystyrene, biodegradable polymers, liposomes, alginate, chitosan. albumin-drug complexes and quantum dots. In embodiments these will be the substrate material.

Liposomal nanoparticles are known delivery vehicles which can encapsulate therapeutic payloads and can display ligands on their surface. Suitable liposome formulations would be known to those in the art and appropriate chemistry to attach ligands (in the present invention a sialic acid or an analog thereof) to the surface of such liposomes is known. In embodiments, a linker attached to a sialic acid to be immobilised on the surface of the nanoparticle, for example a liposome. The linker can be provided between the sialic acid and the substrate surface.

Suitably in embodiments nanoparticles or microparticles can be parenerally administered. After parentaeral administration, nanoparticles can selectively accumulate in particular tissues or body locations. In embodiments, nanoparticles can deliver a therapeutic payload to the cell or tissue. In embodiments, nanoparticles can access diseased tissue through an enhanced permeability and retention effect.

In embodiments, substrate, for example a microparticle or nanoparticle, may be a polymeric particle, in particular a particle may be formed from a biodegradable polyester such as poly(lactide) (PLA), poly(glycolide)(PGA), poly(butyl cyanoacrylate) (PBCA), or N-(2-hydroxypropyl)methacrylamide (HPMA) copolymers. A pharmaceutical composition of the invention is formulated to be compatible with its intended route of administration. Examples of routes of administration include parenteral, e.g. intravenous, intradermal, subcutaneous, oral (for example inhalation), transdermal (topical), transmucosal, and rectal administration and poly(lactic-co-glycolic acid) (PLGA), which have been used in pharmaceutical and biomedical applications. Suitable polymers for use as a substrate, wherein the substrate can form a nanoparticle or a medical device will be known in the art. In embodiments, a polymeric particle can be formed of poly(lactic-co-glycolic acid) (PLGA).

Although PLGA polymers can possess free terminal carboxylic groups, many of these can be buried in the particle matrix and not be available for binding on the surface of the particle. In embodiments, more carboxylic groups may be introduced into the particle by providing a second polymer or copolymer surfactant or coating in addition to the first PGLA polymer or copolymer of the particle. Suitably the second polymer or copolymer can be branched or linear and can have a plurality of terminal alkyl groups wherein an alkyl group contains only carbon and hydrogen and forms the homologous series with the general formula $C_nH_{2n+1}$. In embodiments of the invention, the sialic acid molecules or analogs can be attached to the particle, for example a polymeric nanoparticle, via a covalent linkage.

In embodiments the substrate can be polymer which comprises sialic acid at a concentration in the range 1 ng/mg of sialic acid to polymer to 1 mg/mg of sialic acid to polymer, preferably 10 ng/mg to 100 microgram/mg, and most preferably 10 to 15 micrograms of sialic acid per mg of polymer. In embodiments a device can be coated with such a substrate. In alternative embodiments a device can be formed from a polymer, for example wherein the device is a microparticle or nanoparticle, wherein sialic acid is provided in the polymer at a concentration in the range 1 ng/mg of sialic acid to polymer to 1 mg/mg of sialic acid to polymer, preferably 10 ng/mg to 100 microgram/mg, and most preferably 10 to 15 micrograms of sialic acid per mg of polymer.

According to a second aspect of the present invention there is provided a method of treatment of inflammatory disease in a subject in need thereof, said method comprising administering to a subject sialic acid or an analog thereof, wherein the sialic acid or the analog is presented on a substrate such that a pro-inflammatory immune response is suppressed or an anti-inflammatory immune response is increased in the subject.

In embodiments the substrate can be a drug delivery device, for example a microparticle or a nanoparticle. In embodiments the drug delivery device can be adapted to target a cell comprising a siglec receptor to induce activation of the siglec receptor.

Suitably said method may comprise:

identifying a subject having a pro-inflammatory immune response and/or suffering from a disorder associated with or caused by a pro-inflammatory immune response or at risk of developing a pro-inflammatory immune response or a disorder associated with or caused by a pro-inflammatory immune response;

administering to a subject sialic acid or analogs thereof, wherein the sialic acid or analogs are presented on a substrate.

In embodiments the substrate can be a drug delivery device, preferably a nanoparticle to which the sialic acid or analogs thereof are bound.

Alternatively the method may comprise:

identifying a subject having a pro-inflammatory immune response and/or suffering from a disorder associated with or caused by a pro-inflammatory immune response or at risk of developing a pro-inflammatory immune response or a disorder associated with or caused by a pro-inflammatory immune response; and recommending administration of sialic acid or analogs thereof, wherein the sialic acid or analogs are presented on a substrate, for example a drug delivery device, preferably a nanoparticle to which the sialic acid or analogs thereof are bound.

In embodiments the method can be used to treat a subject with cancer, in particular for the treatment of acute myeloid leukaemia.

In embodiments the method can be used to treat a subject with pulmonary disease. Pulmonary disease can include inflammatory and non-inflammatory conditions of the lung, including Tuberculosis (TB), Chronic Obstructive Pulmonary Disorder (COPD), asthma, acute lung injury, acute respiratory distress syndrome, cystic fibrosis, bronchiectasis, pulmonary fibrosis and other forms of interstitial lung disease, pulmonary vascular disease In embodiments the method can be used for the treatment of diseases including; rheumatoid arthritis, Crohn's disease, ulcerative colitis, septic shock, cardiac and vascular disease, acute and chronic renal injury from a variety of causes, various nasal and chronic skin diseases including dermatitis, auto-immune conditions such as diabetes, SLE, and multiple sclerosis.

In particular embodiments, the sialic acid or analogs thereof presented on a substrate are provided as a nanoparticle. Suitably such a nanoparticle can be used to treat inflammatory disease, for example pulmonary or systemic inflammation, tissue rejection and reperfusion injury.

Accordingly there is provided a method of prophylaxis and/or treatment of an immune-mediated condition, the method comprising:

administering sialic acid or analogs thereof presented by a substrate, preferably a nanoparticle, such that a pro-inflammatory immune response is a cell is suppressed or an anti-inflammatory immune response in increased in the subject.

There is provided a composition comprising sialic acid or analogs thereof presented on a substrate, preferably a nanoparticle, for use in the treatment of inflammatory disease.

There is provided the use of sialic acid or analogs thereof presented on a substrate, preferably a nanoparticle in the preparation of a medicament for the treatment of inflammatory disease.

In embodiments the method can be used to treat a subject with cancer, in particular for the treatment of acute myeloid leukaemia. In embodiments the method can be used to treat a subject with pulmonary disease. Pulmonary disease can include inflammatory and non-inflammatory conditions of the lung, including Tuberculosis (TB), Chronic Obstructive Pulmonary Disorder (COPD), asthma, acute lung injury, acute respiratory distress syndrome, cystic fibrosis, bronchiectasis, pulmonary fibrosis and other forms of interstitial lung disease, and pulmonary vascular disease. In embodiments the method can be used for the treatment of diseases including; rheumatoid arthritis, Crohn's disease, ulcerative colitis, septic shock, cardiac and vascular disease, acute and chronic renal injury from a variety of causes, various nasal and chronic skin diseases including dermatitis, auto-immune conditions such as diabetes, SLE, systemic inflammation, tissue rejection and reperfusion injury and multiple sclerosis.

As part of the invention, the inventors have determined a facile approach to the formulation of nanoparticles comprising sialic acid or analogs thereof which can induce activation of a siglec receptor such that the receptor is internalised into the cell and production of a pro-inflammatory cytokine, for example TNF-alpha, by the cell is inhibited thereby suppressing a pro-inflammatory immune response.

Accordingly, a third aspect of the present invention provides a method for producing a substrate coated with or conjoined to sialic acid or a sialic acid analog, for example to provide a drug delivery device or implanted medical device, wherein the method comprises:

- activating a polymer forming a substrate, for example a drug delivery device or an implantable medical device or coating a drug delivery device or implantable medical device,
- providing sialic acid solution to the activated polymer substrate, for example drug delivery device or implantable medical device, and
- associating the sialic acid to the polymer substrate,
- removal of excess unconjugated sialic acid from the activated substrate, for example, drug delivery device or implantable medical device.

In embodiments, the method can comprise the steps of activating the substrate, providing the sialic acid or analog thereof and associating the sialic acid to the substrate. In embodiments the sialic acid can be associated to the substrate via an ester bond.

In embodiments sialic acid, for example alpha 2-8 diAcetylneuraminic acids, can be conjugated to a substrate, for example a nanoparticle using carbodiimide chemistry.

In a particular embodiment, wherein the substrate, for example a drug delivery device or implantable medical device is a nanoparticle, formation can comprise, dissolving 20 mg of poly(lactic-co-glycolic acid) (PLGA) in DCM and acetone then injecting this, under moderate stirring, into ice-cold solution containing 2.5% (w/v) PVA and 45% (w/v) MgCl2.6H2O in pH 5 MES buffer, sonicating both phases in an ice bath, adding 2.5% (w/v) PVApH5 MES buffer solution under moderate stirring and allowing organic solvents to evaporate. The nanoparticles can then be centrifuged at 85 000×g for 10 minutes at 4° C., and washed using suspension-spin cycles with pH5 MES buffer prior to resuspension to give 5 mg PLGA ml-1 in ph5 MES buffer solution.

In embodiments, nanoparticle conjugation can comprise, adding 200 μl of 0.1 M 1-Ethyl-3-[3-dimethylaminopropyl] carbodiimide Hydrochloride (EDC) to an equal amount (200 μl) of 0.7 M N-hydroxysuccinimide (NHS), both dissolved in pH 5.0 MES buffer, adding this to a nanoparticle suspension, wherein the nanoparticle suspension formed can be kept at room temperature for 1 hour under moderate stirring, and centrifuging the suspension to eliminate unused adsorbent reagents. A 1 ml suspension of 1 mg $mL^{-1}$ activated nanoparticles in PBS can be added to 10 μl of 10.0 mg $mL^{-1}$ of a α,2-8-NANA solution and incubated at 4 degrees C. overnight. Finally, solutions can be centrifuged at 20.000×g for 1 hour at 10 degrees C. and resuspended in PBS to remove excess of unconjugated α,2-8-NANA.

According to a fourth aspect of the present invention, there is provided a substrate comprising sialic acid or an analog thereof, in particular wherein said substrate is formed by a method according to the third aspect of the invention, wherein the substrate is adapted to target a cell comprising a siglec receptor and inhibit production of pro-inflammatory cytokines within the cell or increase production of anti-inflammatory cytokines within the cell thereby suppressing a pro-inflammatory immune response.

As indicated above, methods to determine the level of a pro-inflammatory cytokine within a cell or an anti-inflammatory cytokine in a cell are well known in the art. Thus, the skilled person would be able to functionally determine if the substrate can inhibit production of pro-inflammatory cytokines within the cell or increase production of anti-inflammatory cytokines within the cell thereby suppressing a pro-inflammatory immune response.

The substrate can present a sialic acid or analog thereof on a surface of the substrate such that the sialic acid or an analog can be bound by a siglec receptor. The sialic acid can be immobilised on the surface of the substrate such that the sialic acid is provided at a density concentration to inhibit production of pro-inflammatory cytokine or increased production of anti-inflammatory cytokine.

The substrate can form or coat, for example a drug delivery device or implantable medical device. In embodiments the substrate can be coated with sialic acid or a sialic acid analog can be coated onto a device. In alternative embodiments the substrate can be conjoined to sialic acid or a sialic acid analog and form the device.

In embodiments the substrate can be polymer which comprises sialic acid at a concentration in the range 1 ng/mg of sialic acid to polymer to 1 mg/mg of sialic acid to polymer, preferably 10 ng/mg to 100 microgram/mg, and most preferably 10 to 15 micrograms of sialic acid per mg of polymer. In embodiments a device can be coated with such a substrate. In alternative embodiments a device can be formed from a polymer, for example wherein the device is a microparticle or nanoparticle, wherein sialic acid is provided in the polymer at a concentration in the range 1 ng/mg of sialic acid to polymer to 1 mg/mg of sialic acid to polymer, preferably 10 ng/mg to 100 microgram/mg, and most preferably 10 to 15 micrograms of sialic acid per mg of polymer.

In embodiments, a drug delivery device of the present invention can further comprise a therapeutic drug entrapped or adsorbed in the device, for example the device can be a nanoparticle or microparticle, such that the therapeutic drug is delivered to a targeted cell expressing a siglec receptor. Appropriate sialic acids present on the nanoparticle can be used to target the device, to particular cells bearing particular siglec receptors.

In particular embodiments a drug delivery device such as a nanoparticle of the invention can further comprise at least one of an antibiotic, an anti-viral agent, an anti-inflammatory, a cytokine, a cytokine inhibitor, an immunomodulator, an immunotoxin, an anti-angiogenic agent, an anti-hypertensive, an anti-oedema agent, a radiosenstiser, an oligonucleotide comprising DNA or RNA, a peptide, an anti-cancer agent or combinations thereof. Suitably, an anti-cancer agent may be selected from at least one of cytarabine, daunorubicin, etoposide, fludarabine, idarubicin, doxorubicin, deoxydoxorubicin, morpholinodoxorubicin, 5-fluorouracil, captothecin or a derivative thereof, methotrexate or a derivative thereof, cisplatin, metronicdazole, camptothecin or a combination thereof.

Additionally, a variety of established and novel drugs may be delivered by a delivery device comprising a substrate, for example the surface of a nanoparticle, conjoined to sialic acid or an analog thereof. In particular a drug may be delivered to the lung by a device on the invention. Suitably said drugs may comprise beta-agonists, antibiotics, anti proteases, anti-inflammatory including steroids and statins, recombinant human proteins, such as, but not limited to, keratinocyte growth factor monoclonal antibodies and vasoactive drugs.

Suitably, a drug delivery device of the present invention, for example a microparticle or nanoparticle, may be administered to a subject along with a pharmaceutical carrier or excipient, for example to aid delivery of the nanoparticle to particular cell types.

A fifth aspect of the present invention provides a pharmaceutical composition comprising a therapeutically effective amount of a drug delivery device comprising a substrate conjoined to sialic acid or an analog thereof as described in the fourth aspect of the invention.

A substrate, for example a drug delivery device, coated with or conjoined to sialic acid or a sialic acid analog such that the drug delivery device is adapted to target a cell comprising a siglec receptor and inhibit production of pro-inflammatory cytokines and/or increase anti-inflammatory cytokines can be provided with a pharmaceutically acceptable diluent, excipient or carrier. In embodiments, a drug delivery device can be a nanoparticle coated with the substrate to which sialic acid or a sialic acid analog is bound.

The present inventors have determined that sialic acid coated PLGA nanoparticles are stable to freeze drying which allows them to be usefully employed for the pulmonary delivery of drugs. Suitably, for the treatment of inflammatory diseases of the lung and other similar diseases, it may be preferable to provide the nanoparticles of the present invention as an aerosol formulation.

The pharmaceutical compositions of the invention are preferably administered to an individual in a “therapeutically effective amount”, this being sufficient to show benefit to the individual. The actual dosage regimen will depend on a number of factors including the condition being treated, its severity, the patient being treated, the agent being used, and will be at the discretion of the physician.

The optimal dose can be determined by physicians based on a number of parameters including, for example, age, sex, weight, severity of the condition being treated, the active ingredient being administered and the route of administration.

Preferred features and embodiments of each aspect of the invention are as for each of the other aspects mutatis mutandis unless context demands otherwise.

Each document, reference, patent application or patent cited in this text is expressly incorporated herein in their entirety by reference, which means it should be read and considered by the reader as part of this text. That the document, reference, patent application or patent cited in the text is not repeated in this text is merely for reasons of conciseness.

Throughout the specification, unless the context demands otherwise, the terms ‘comprise’ or ‘include’, or variations such as ‘comprises’ or ‘comprising’, ‘includes’ or ‘including’ will be understood to imply the includes of a stated integer or group of integers, but not the exclusion of any other integer or group of integers.

Embodiments of the present invention will now be described by way of example only with reference to the accompanying figures in which:

FIG. 1 (A) provides a schematic representation of a PGLA nanoparticle with alpha 2-8 diacetylneuraminicacids (sialic acid) conjucated on its surface; 1 (B) illustrate PLGA and 1 (C) illustrates alpha 2-8 diacetylneuraminic acid.

FIG. 2 provides a table indicating typical conjugation efficiencies of the disialic acids to the nanoparticles and quantities per mg PLGA successfully attached.

Figure 3:
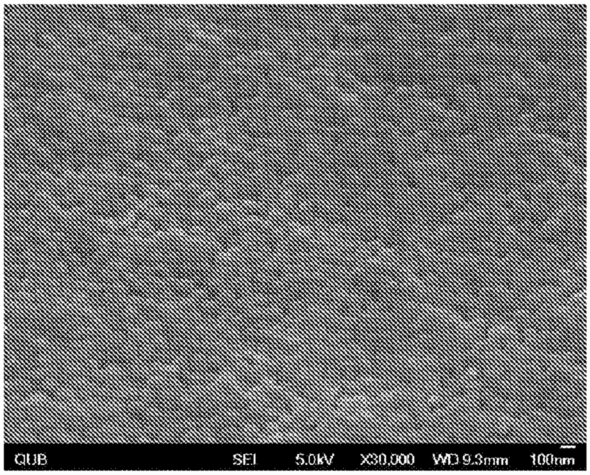

FIG. 3 illustrates (A) Particle Size and Zeta Potential of PLGA nanoparticles (NP) conjugated or non conjugated with alpha 2-8 diAcetylneuraminic acid (a sialic acid) wherein NP were prepared using nanoprecipitation/salting out formulation and conjugated to alpha 2-8 diAcetylneuraminic acids using carbodiimide chemistry. NP size and zeta potential were measured using photon correlation spectroscopy and laser Doppler anemometry, respectively (ZetaSizer 3000 HS, Malvern instruments, UK); (B) Illustrates SEM of freeze-dried nanoparticles mounted onto aluminium stubs and coated in gold. Nanoparticles were visualised using a scanning electron microscope. n=3. Scale bar=100 nm.

Figure 4:
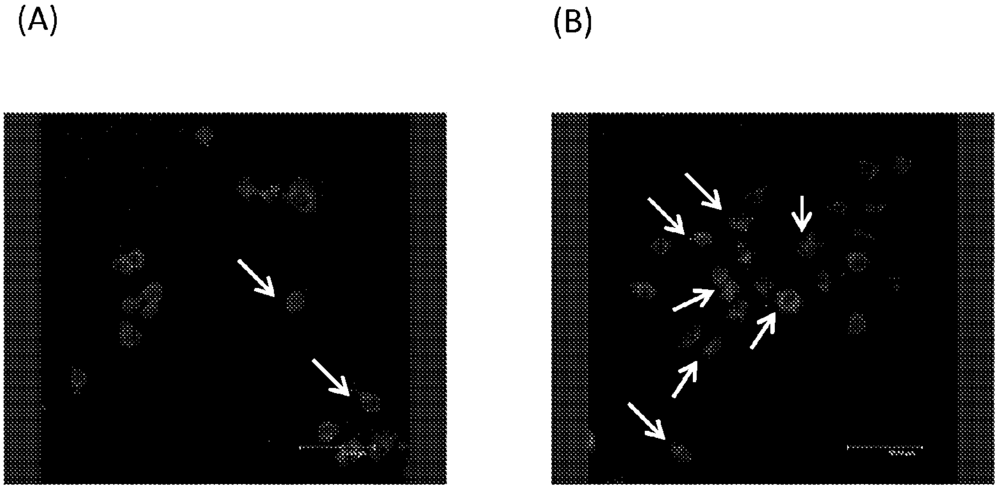

FIG. 4 shows confocal fluorescence microscopy images for Raw 264 cells incubated with (A) a 25 μL suspension of naked coumarin 6-loaded NP,(B) a 25 μL suspension of coumarin 6-loaded NP conjugated with alpha 2-8 di-acetylneuraminic acids wherein cells were exposed to NP dispersions over a 90-min incubation period at 37 C and 5% CO2 The cells were washed three times with ice-cold PBS then pH8 HEPES buffer following with an 15 min incubation with 1/200 of TO-PRO®-3 iodide (invitrogen) solution and finally washed three times with ice-cold PBS. Observations were done using confocal scanning laser microscopy (LeicaConfocal TCS Sp2, Germany) (green: coumarin-6 loaded NP) (blue: topo3 staining of the nucleus). White arrows highlight green labelled nanoparticles adhering to the cells.

Figure 5:
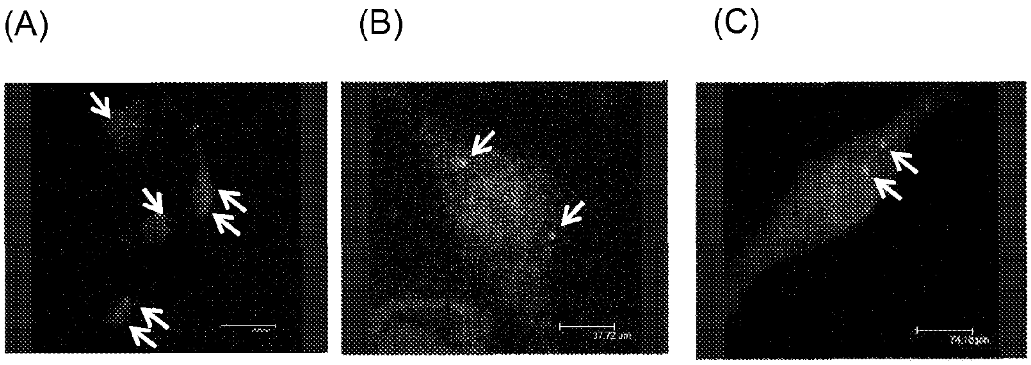

FIG. 5 shows representative confocal fluorescence microscopy images for Raw 264 cells incubated with a 50 μL suspension of Nile red-loaded NP conjugated with alpha 2-8 di-acetylneuraminic acids wherein cells were exposed to NP dispersions over a 90-min incubation period at 37° C. and 5% CO2. During the last 10 minutes of incubation the cells were also incubated with calceinAM (invitrogen). The cells were washed three times with ice-cold PBS then pH8 HEPES buffer following a 15 min incubation with 1/200 of TO-PRO®-3 iodide (invitrogen) solution and finally washed three times with ice-cold PBS. Observations were done by confocal scanning laser microscopy (LeicaConfocal TCS Sp2, Germany) (green: calceinAM staining of the cytoplasm)

(Red: Nile red labelled nanoparticles) (blue: topo3 staining of the nucleus). White arrows highlight the internalised red labelled nanoparticles.

Figure 6:
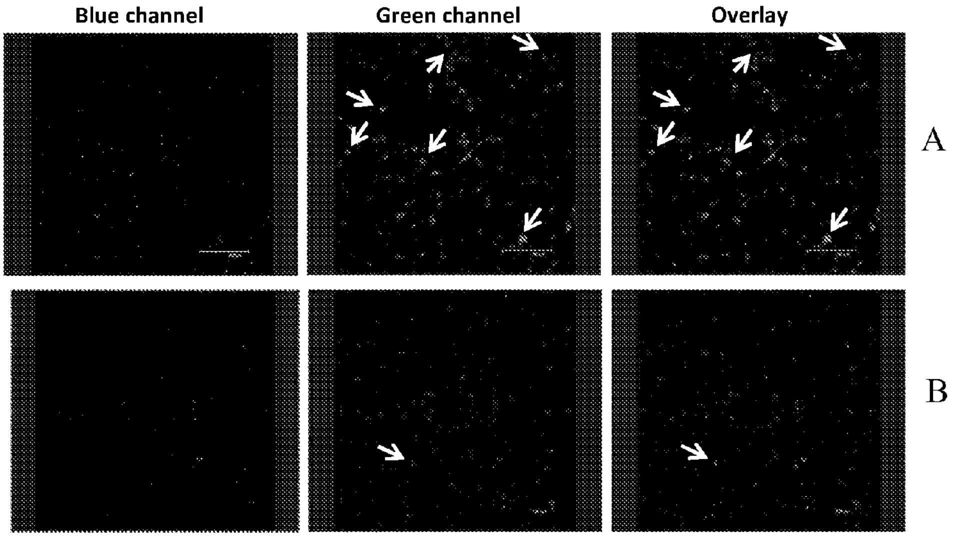

FIG. 6 illustrates confocal fluorescence microscopy images for (A) Raw 264 cells incubated with a 25 μL suspension coumarin 6-loaded NP conjugated with sialic acid (green), (B) Raw 264 cells were preincubated for 3 h with free anti-Siglec E antibodies and then incubated with coumarin 6-loaded nanoparticles conjugated with sialic acid (green). Cells were exposed to NP dispersions over a 90-min incubation period at 37° C. and 5% CO2. The cells were washed three times with ice-cold PBS then pH8 HEPES buffer following with an 15 min incubation with 1/200 of TO-PRO®-3 iodide (invitrogen) solution and finally washed three times with ice-cold PBS. Observations were done using confocal scanning laser microscopy (LeicaConfocal TCS Sp2, Germany) (green: coumarin-6 loaded NP) (blue: topo3 staining of the nucleus). White arrows highlight green labelled nanoparticles binding to the cells. This shows that the sialic acid nanoparticle targeting is siglec E dependent.

Figure 7:
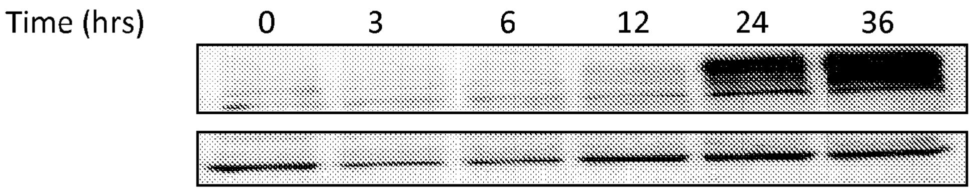

FIG. 7 shows upregulation of Siglec-E (upper pane) over time in response to 1 ng/ml LPS wherein $6\times10^5$ murine bone marrow derived macrophages were stimulated with 1 ng/ml LPS for 0, 3, 6, 12 or 24 hrs to upregulate Siglec-E and cells were lysed in 2× laemelli buffer and blotted with anti-Siglec-E specific antibody and appropriate secondary antibody. Lower pane shows loading controls (gamma tubulin).

Figure 8:
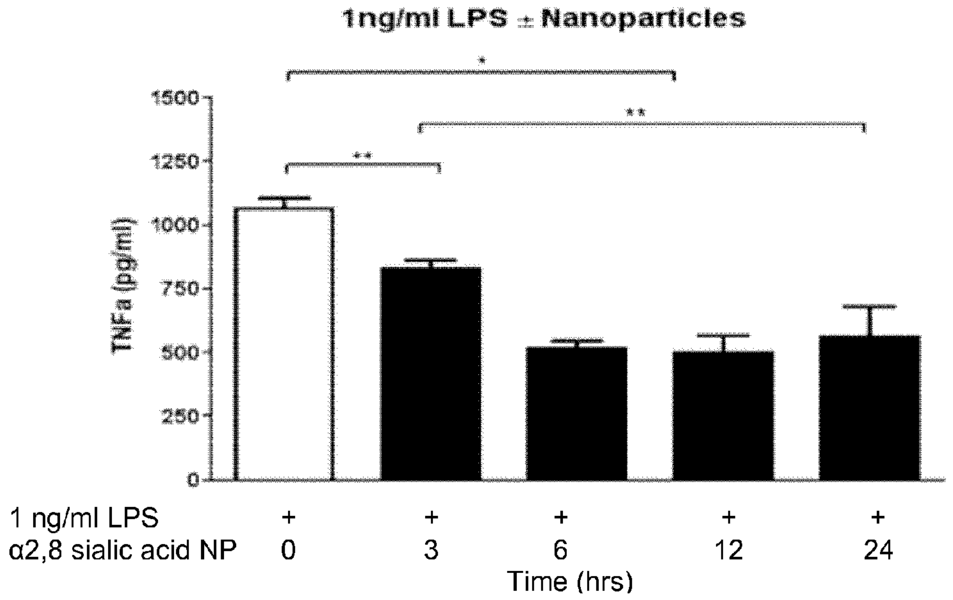

FIG. 8 shows differential inhibition of the inflammatory response by nanoparticle incubation period wherein $6\times10^5$ murine bone marrow derived macrophages were stimulated with 1 ng/ml LPS overnight to upregulate Siglec-E. Cells were washed twice in serum-free DMEM prior to resting for 2 hr. Cells were re-stimulated with 1 ng/ml LPS±α2,8 sialic acid conjugated PLGA nanoparticles for 0, 3, 6, 12 or 24 hr. TNFα was measured by ELISA. Statistical significance was determined by ELISA. P=0.001

Figure 9:
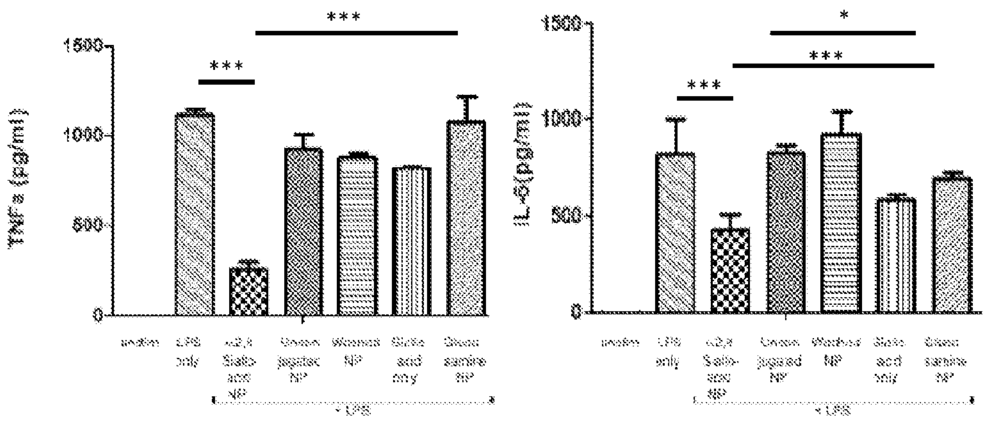

FIG. 9 illustrates reduction of TNFα and IL-6 production from C57bl/6 bone marrow derived macrophages (BMDM) incubated with LPS and α2,8 sialic acid conjugated PLGA nanoparticles. The BMDM were stimulated with 1 ng/ml LPS overnight to up-regulate Siglec-E. Cells were washed twice in serum-free DMEM prior to resting for 2 hr. Cells were re-stimulated with 1 ng/ml LPS±α2,8 sialic acid conjugated PLGA nanoparticles (NP) or appropriate controls—Unconjugated (nude) NP, Sialic acid washed, but unconjugated NP, Sialic acid at same concentration as NP or nanoparticles conjugated to the non-Siglec binding glucosamine. TNFα and IL-6 was measured by ELISA. One way ANOVA was used to determine significance. P=0.001(***) or 0.039 (*) shows C57bl/6 BMDM stimulated with LPS and α2,8 sialic acid conjugated PLGA nanoparticles results in a decreased inflammatory response.

Figure 10:
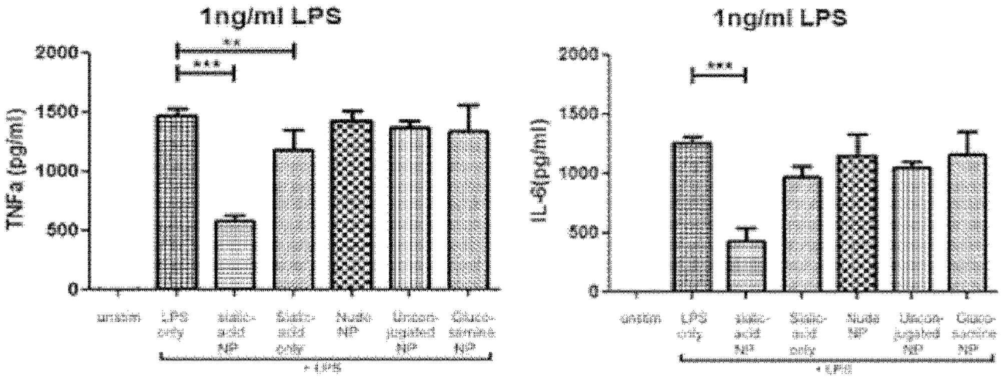

FIG. 10 illustrates sialic acid conjugated nanoparticles are stable to lyophilization wherein treatment of C57bl/6 peritoneal macrophages incubated with LPS and reconstituted α2,8 sialic acid conjugated PLGA nanoparticles results in a decreased inflammatory response. $6\times10^5$ C57bl/6 peritoneal macrophages were stimulated for 6 hr with 1 ng/ml LPS±reconstituted α2,8 sialic acid conjugated PLGA nanoparticles (NP) or appropriate reconstituted controls—Unconjugated (nude) NP, Sialic acid washed, but unconjugated NP, Sialic acid at same concentration as NP or nanoparticles conjugated to the non-Siglec binding glucosamine. TNFα and IL-6 was measured by ELISA. One way ANOVA was used to determine significance. P=0.001.

Figure 11:
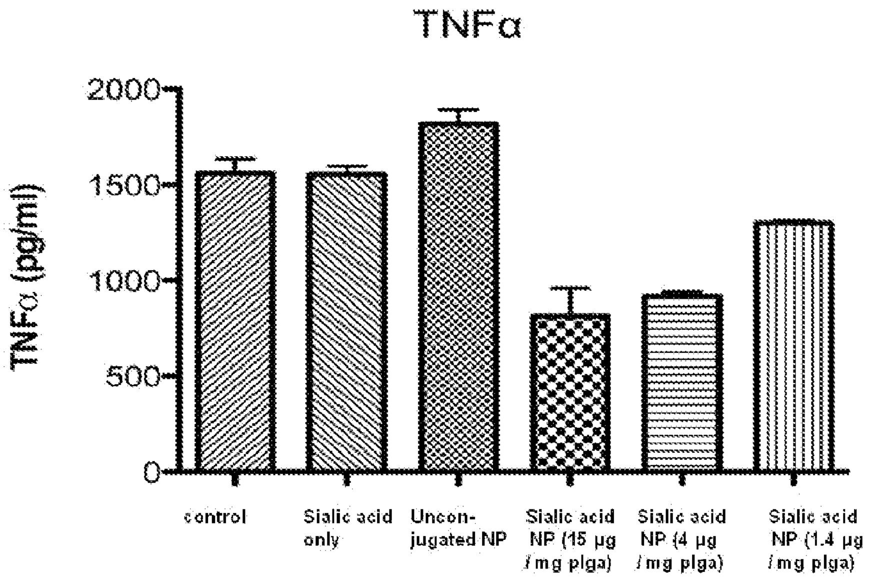

FIG. 11 illustrates the reduction in inflammatory response is sialic acid conjugation dose dependent wherein C57bl/6 peritoneal macrophages incubated with LPS and various PLGA nanoparticles conjugated with different amount of α2,8 sialic acid results in a decreased inflammatory response dependent on the concentration of sialic acid bound to the NP. With $6\times10^5$ C57bl/6 peritoneal macrophages were stimulated for 6 hr with 1 ng/ml LPS±α2,8 sialic acid conjugated PLGA nanoparticles (sialic acid) or appropriate reconstituted controls—Unconjugated (nude) NP, free Sialic (unconjugated-sialic acid), TNFα was measured by ELISA.

Figure 12:
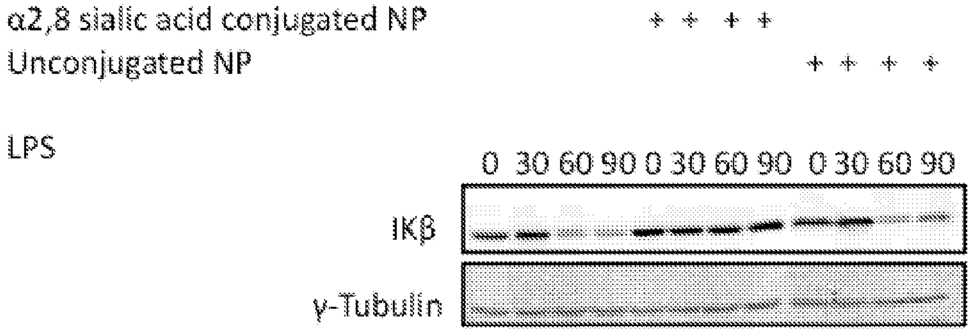

FIG. 12 illustrates THP-1 cells—a human monocytic cell line exhibit reduced Ikβ degradation when co-stimulated with α2,8 sialic acid conjugated nanoparticles; indicating an inhibited pro-inflammatory response wherein $1\times10^6$ THP-1 cells were stimulated with 100 ng/ml LPS for 0, 30, 60 and 90 minutes. Concurrently, the cells were also treated with α2,8 sialic acid conjugated NP, or unconjugated NP. Cells were lysed directly in Laemelli buffer and whole cell lysates blotted for IKβ and gamma-tubulin.

Figure 13:
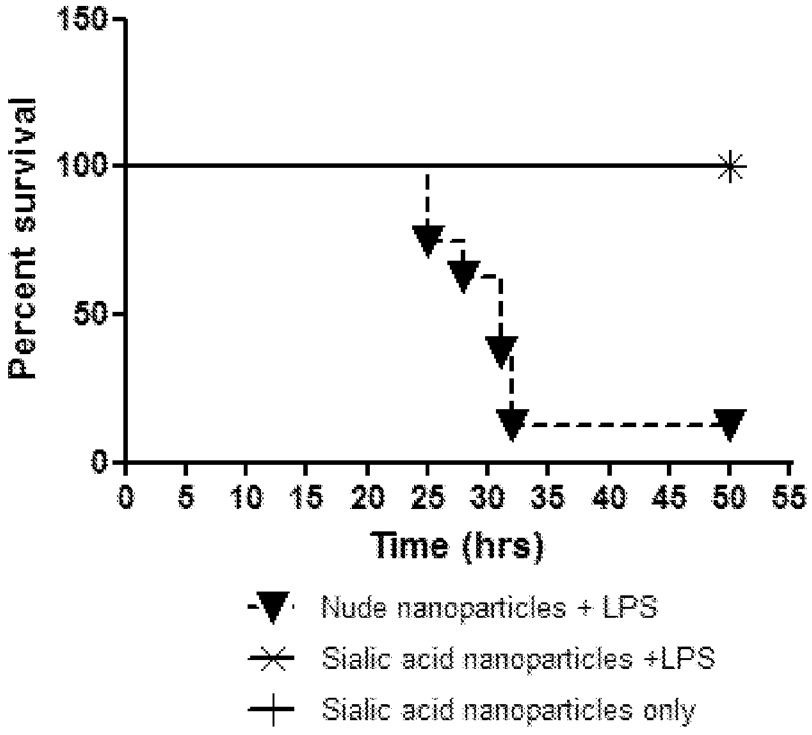

FIG. 13 illustrates sialic acid presented on nanoparticles reduce inflammation in vivo wherein C57bl/6 mice were treated with peritoneal injections of (6 mg/kg) LPS and/or 2 mg of solution of PLGA nanoparticles; α2,8 sialic acid conjugated PLGA nanoparticles (sialic acid) or Unconjugated (nude) NP and a Log Rank Chi square Test was used to determine significance (N=8 and P=0.009).

Figure 14:
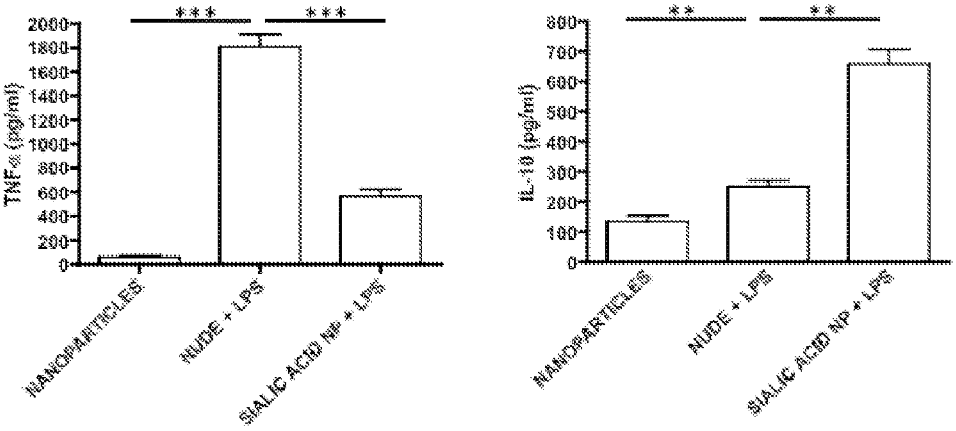

FIG. 14 illustrates sialic acid presented on nanoparticles reduce inflammation in vivo wherein C57bl/6 mice were treated with peritoneal injections of (6 mg/kg) LPS and/or 2 mg of solution of PLGA nanoparticles; α2,8 sialic acid conjugated PLGA nanoparticles (sialic acid) or Unconjugated (nude) NP. At t=24 h. Blood samples were taken by tail vein puncture and TNFα and IL-10 over 24 hrs were measured by ELISA. One way ANOVA was used to determine significance (*=0.001 and =<0.01).

Figure 15:
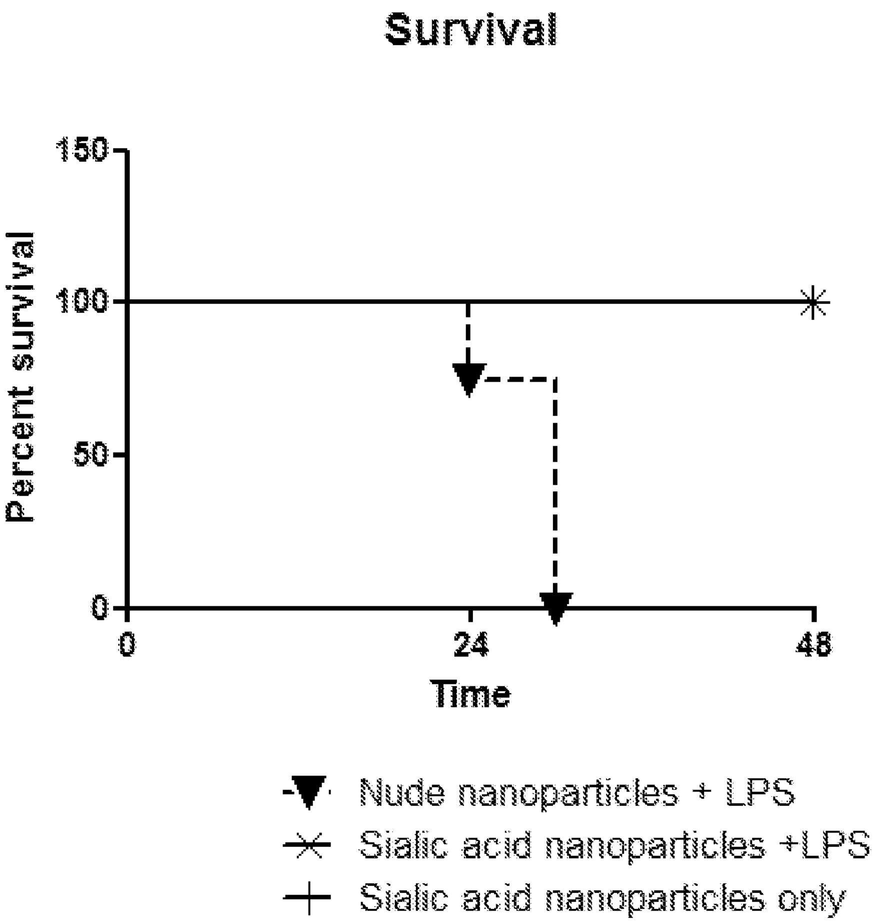

FIG. 15 illustrates that sialic acid presented on nanoparticles can rescue mice from a lethal dose of LPS wherein C57bl/6 mice were treated with peritoneal injections of (6 mg/kg) LPS or PBS, and two hours later 2 mg of solution of PLGA nanoparticles; α2,8 sialic acid conjugated PLGA nanoparticles (sialic acid) or Unconjugated (nude) NP were injected through peritoneal injections; (n=4 per arm of study).

Figure 16:
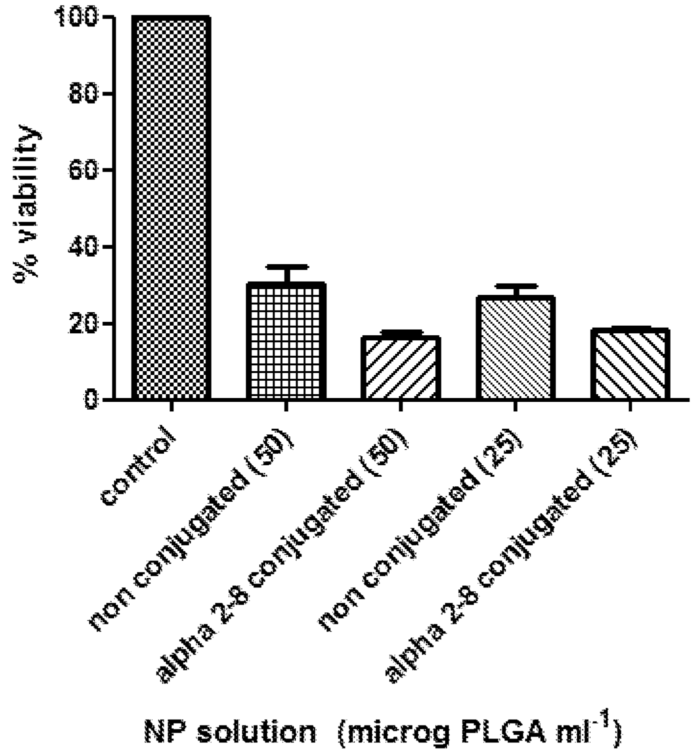

FIG. 16 illustrates sialic acid presented on nanoparticles can be used to target leukemic cells in a chemotherapy targeting strategy wherein CPT-encapsulated PLGA show improved toxicity with incubation of THP1 with 2,8NANA targeting. THP1 cells were plated overnight then incubated 12 hours with: PLGA CPT loaded nanoparticles nude (CPT-NP) or conjugated to 2,8NANA (CPT-NANA) sialic acid conjugated. After incubation cells were washed and re-incubated in new cell media for a further 60 hours. (results are mean±SD, n=6, * (P<0.05).

EXAMPLE 1

Preparation of PLGA Nanoparticles 20 mg of poly(lactic-co-glycolic acid) (PLGA) was dissolved in 200 μl (DCM) and 600 μl acetone then injected under moderate stirring into 3.0 ml of ice-cold solution containing 2.5% (w/v) (PVA) and 45% (w/v) $MgCl_2.6H_2O$ in ph5 MES buffer. Both phases were then sonicated in an ice bath at 20 mW. An additional 5.0 ml of 2.5% (w/v) PVA ph5 MES buffer solution was finally added under moderate stirring. Samples were left stirring overnight to allow organic solvent evaporation. Nanoparticles were centrifuged at 85000×g for 10 minutes at 4 degrees C., then washed using suspension-spin cycles with pH5 MES buffer. Nanoparticle pellets were resuspended to give 5 mg PLGA $ml^{-1}$ in pH5 MES buffer solution prior to further use.

EXAMPLE 2

Nanoparticle Activation and Conjugation with Sialic Acid

Nanoparticle activation to allow conjugation to the sialic acid was achieved by adding 200 μl of 0.1 M 1-Ethyl-3-[3-dimethylaminopropyl]carbodiimide Hydrochloride (EDC) and 200.0 μl of 0.7 M N-hydroxysuccinimide (NHS), both dissolved in pH 5.0 MES buffer, to the nanoparticulate suspension, which was kept at room temperature for 1 hour under moderate stirring. After centrifugation to eliminate unused adsorbent reagents, nanoparticles were resuspended at 1 mg $ml^{-1}$ in PBS. Sialic acid solution (100 μl of 1.0 mg $ml^{-1}$ solution) was added to a 1 ml suspension of 1 mg $ml^{-1}$ activated nanoparticles and incubated at 4 degrees C. overnight. Finally, solutions were centrifuged at 10000×g for 2 hour at 10 degrees C. and resuspended in PBS to remove excess of unconjugated sialic acid.

Particle Size and Zeta Potential of PLGA nanoparticles conjugated or non conjugated with alpha 2-8 diAcetylneuraminicacids (a sialic acid) were measured using photon correlation spectroscopy and laser Doppler anemometry, respectively (ZetaSizer 3000 HS, Malvern instruments, UK) and the results are provided in table 2.

Nanoparticles of around 150 nm in diameter and prepared with 15 μg of sialic acid per mg of polymer are discussed further in the examples provided.

TABLE 2

| | NP non conjugated | NP conjugated with alpha 2-8 di Acetylneuraminic acids |
|---|---|---|
| Size | 151 nm ± 10 | 152 nm ± 13 |
| Zeta potential | 0.4 mv ± 0.4 | 0.3 mv ± 0.2 |

EXAMPLE 3

Sialic Acid Conjugation Facilitates Specific Targeting to Myeloid Cell Line

FIG. 4 shows Raw 264 cells incubated with (A) a 25 μl suspension of naked coumarin 6-loaded nanoparticles at 100 micrograms per ml and (B) a 25 μl suspension of coumarin 6-loaded nanoparticles conjugated with alpha 2-8 di-acetylneuraminic acids. Cells were exposed to the nanoparticle dispersions over a 90-min incubation period at 37 degrees C. and 5% $CO_2$. The cells were washed three times with ice-cold PBS then pH8 HEPES buffer followed with 15 minutes incubation with 1/200 of TO-PRO®-3 iodide (invitrogen) solution and finally washed three times with ice-cold PBS. Observations were done using confocal scanning laser microscopy (LeicaConfocal TCS Sp2, Germany) (green: coumarin-6 loaded NP) (blue: topo3 staining of the nucleus). White arrows highlight green labelled nanoparticles.

EXAMPLE 4

Sialic Acid Nanoparticles are Internalised by Cells

As shown in FIG. 5, cells were exposed to nanoparticle dispersions over a 90-min incubation period at 37 degrees C. and 5% $CO_2$ and during the last 10 minutes of incubation the cells were also incubated with calceinAM (invitrogen). The cells were washed three times with ice-cold PBS then pH8 HEPES buffer followed by 15 minutes incubation with 1/200 of TO-PRO®-3 iodide (invitrogen) solution and finally washed three times with ice-cold PBS. Observations were done by confocal scanning laser microscopy (LeicaConfocal TCS Sp2, Germany) (green: calceinAM staining of the cytoplasm) (Red: Nile red labelled nanoparticles—red labelled nanoparticle are highlighted with arrows) (blue: topo3 staining of the nucleus).

EXAMPLE 5

Siglec Receptors can be Up-Regulated by Inflammatory Stimuli (LPS)

As shown in FIG. 7, $6\times10^5$ murine bone marrow derived macrophages were stimulated with 1 ng/ml LPS for 0, 3, 6, 12 or 24 hours to upregulate Siglec-E. Cells were lysed in 2× laemelli buffer and blotted with anti-Siglec-E specific antibody and appropriate secondary antibody.

EXAMPLE 6

Sialic Acid Nanoparticles Inhibit LPS-Induced Inflammatory Response (TNF Alpha Expression)

$4\times10^4$/well murine bone marrow derived macrophages were stimulated with 1 ng/ml LPS overnight to up-regulate Siglec-E; cells were washed twice in serum-free DMEM prior to resting for 2 hr and then cells were re-stimulated with 1 ng/ml LPS±25 μg/ml α2,8 sialic acid conjugated PLGA nanoparticles for 0, 3, 6, 12 or 24 hr with TNFα being measured by ELISA (Statistical significance was determined by one way ANOVA and post hoc Tukey test. P=0.001) (FIG. 5) TNF alpha was found to be reduced in cells treated with α2,8 sialic acid conjugated PLGA nanoparticles.

EXAMPLE 7

C57bl/6 BMDM Incubation with 1 Ng/Ml LPS and 25 μg/Ml α2,8 Sialic Acid Conjugated PLGA Nanoparticles Results in a Decreased Inflammatory Response $4\times10^4$/well C57bl/6 bone marrow derived macrophages were stimulated with 1 ng/ml LPS overnight to up-regulate Siglec-E. Cells were washed twice in serum-free DMEM prior to resting for 2 hr. The results of cells re-stimulated with 1 ng/ml LPS±α2,8 sialic acid conjugated PLGA nanoparticles (NP) or appropriate controls—Unconjugated (nude) nanoparticles, Sialic acid washed—but unconjugated nanoparticles, Sialic acid at same concentration as nanoparticles or nanoparticles conjugated to the non-Siglec binding glucosamine are shown. TNFα and IL-6 was measured by ELISA. One way ANOVA with post-hoc Tukey test was used to determine significance. P=0.001.

It was observed TNF alpha and IL-6 were reduced in cells treated with α2,8 sialic acid conjugated PLGA nanoparticles.

This demonstrates that the provision of nanoparticles or sialic acid alone is insufficient to cause the effect observed and it is the combination of sialic acid bound to the nanoparticles which results in the reduction of TNF alpha and IL-6.

EXAMPLE 8

Sialic-Acid Conjugated Nanoparticles are Stable to Lyophilization

As shown in FIG. 10, $6\times10^5$ C57bl/6 peritoneal macrophages were stimulated for 6 hr with 1 ng/ml LPS±reconstituted α2,8 sialic acid conjugated PLGA nanoparticles (NP) or appropriate reconstituted controls—Unconjugated (nude) nanoparticles, Sialic acid washed, but unconjugated nanoparticles, Sialic acid at same concentration as nanoparticles or nanoparticles conjugated to the non-Siglec binding glucosamine. TNFα and IL-6 were measured by ELISA. One way ANOVA was used to determine significance. P=0.001.

It was observed that even following lyophilisation of sialic acid conjugated nanoparticles, TNF alpha and IL-6 were reduced in cells treated with the previously lypholized α2,8 sialic acid conjugated PLGA nanoparticles.

EXAMPLE 9

2,8 Linked Sialic Acid Conjugated Nanoparticles Prevent IκB Degradation in Human Cells FIG. 12 shows $1\times10^6$ THP-1 cells stimulated with 100 ng/ml LPS for 0, 30, 60 and 90 minutes. Concurrently, the cells were also treated with α2,8 sialic acid conjugated nanoparticles, or unconjugated nanoparticles. Cells were lysed directly in Laemelli buffer and whole cell lysates blotted for IKβ and gamma-tubulin. In those cells treated with α2,8 sialic acid conjugated nanoparticles, IκB degradation was reduced (25 μg/ml final concentration).

EXAMPLE 10

Incubation of THP 1 Cells with α2,8 Sialic Acid Conjugated PLGA Nanoparticles Containing Camptothecin $4\times10^4$ THP 1 cells were incubated with α2,8 sialic acid conjugated PLGA nanoparticles (25 or 50 μg/ml) containing 3 μg camptothecin per mg PLGA and incubations with a control nanoparticle solution and unconjugated nanoparticles were also performed.

As shown in FIG. 16, those nanoparticles including camptothecin and to which α2,8 sialic acid was conjugated caused greatest cell death of the leukaemia cell line when determined over 72 hours.

EXAMPLE 11

In Vivo Studies Illustrating Reduced Inflammatory Response

As illustrated in FIG. 13, in vivo studies were conducted in mice in which peritoneal injections of (6 mg/kg) LPS and/or 2 mg of solution of PLGA nanoparticles as discussed above were administered to the mice. Whilst those mice which were provided with LPS and nude nanoparticles died, those provided with nanoparticles presenting sialic acid and LPS survived. Analysis of the serum cytokines (TNFα and IL-10) over 24 hrs showed that the sialic acid presenting nanoparticles reduced TNFα levels and increased IL-10 levels (see FIG. 14). Moreover, it was found that sialic acid presented on nanoparticles was able to rescue mice from a lethal dose of LPS when the sialic acid presented on nanoparticles were provided to the mice up to 2 hours after administration of the LPS (see FIG. 15).

Although the invention has been particularly shown and described with reference to particular examples, it will be understood by those skilled in the art that various changes in the form and details may be made therein without departing from the scope of the present invention.

The invention claimed is:

1. A method of modulating an inflammatory response in a cell, the method comprising: providing sialic acid presented on a microparticle or nanoparticle to a cell such that a proinflammatory response is suppressed through reduction of TNF alpha levels or an anti-inflammatory response is increased through an increase in IL-10 levels in the cell, and wherein the sialic acid is NeuAcα2-8NeuAc.

2. The method as claimed in claim 1 wherein the nanoparticle or microparticle is formed of poly(lactic-co-glycolic acid) (PLGA).

3. The method as claimed in claim 2 wherein the nanoparticle has a greatest cross-sectional dimension in the range of 130 nm to 170 nm.

4. The method as claimed in claim 1 wherein the microparticle or nanoparticle is a polymer and comprises sialic acid at a concentration in the range 1 ng/mg of sialic acid to polymer to 1 mg/mg of sialic acid to polymer.

5. The method as claimed in claim 1 wherein the microparticle or nanoparticle is a polymer and comprises sialic acid at a concentration in the range 10 ng/mg to 100 microgram/mg of sialic acid to polymer.

6. A method of treating inflammatory disease in a subject in need thereof, said method comprising: administering to the subject sialic acid presented on a microparticle or nanoparticle such that a pro-inflammatory immune response is suppressed through reduction of TNF alpha levels or an anti-inflammatory response is increased through an increase in IL-10 levels in the subject, wherein the sialic acid is NeuAcα2-8NeuAc.

7. The method of claim 6, wherein the inflammatory disease is acute myeloid leukaemia.

8. The method of claim 6, wherein the inflammatory disease is pulmonary disease, preferably inflammatory pulmonary disease.

9. The method of claim 6, wherein the inflammatory disease is selected from Tuberculosis, Chronic Obstructive Pulmonary Disorder (COPD), asthma, acute lung injury, acute respiratory distress syndrome, cystic fibrosis, bronchiectasis, pulmonary fibrosis and other forms of interstitial lung disease, pulmonary vascular disease, rheumatoid arthritis, Crohn's disease, ulcerative colitis, septic shock, cardiac and vascular disease, acute and chronic renal injury, nasal and chronic skin diseases including dermatitis, and auto-immune conditions.

10. The method of claim 9, wherein the auto-immune condition is Diabetes.

11. The method of claim 9, wherein the auto-immune condition is Systemic Lupus Erythematosus (SLE).

12. The method of claim 9, wherein the auto-immune condition is Multiple Sclerosis.

13. The method as claimed in claim 6, wherein the nanoparticle or microparticle is formed of poly(lactic-co-glycolic acid) (PLGA).

14. The method as claimed in claim 6, wherein the nanoparticle has a greatest cross-sectional dimension in the range of 130 nm to 170 nm.

15. The method as claimed in claim 6, wherein the substrate is a polymer and comprises sialic acid or an analog thereof at a concentration in the range 1 ng/mg of sialic acid or an analog thereof to polymer to 1 mg/mg of sialic acid or an analog thereof to polymer.

16. The method as claimed in claim 6, wherein the substrate is a polymer and comprises sialic acid or an analog thereof at a concentration in the range 10 ng/mg to 100 microgram/mg of sialic acid or an analog thereof to polymer.

17. A composition comprising sialic acid presented on a microparticle or nanoparticle for use in the treatment of inflammatory disease such that a proinflammatory response is suppressed through reduction of TNF alpha levels or an anti-inflammatory response is increased through an increase in IL-10 levels, wherein the sialic acid is NeuAcα2-8NeuAc.

* * * * *

UNITED STATES PATENT AND TRADEMARK OFFICE

CERTIFICATE OF CORRECTION

PATENT NO. : 8,962,032 B2
APPLICATION NO. : 13/515884
DATED : February 24, 2015
INVENTOR(S) : Christopher Scott et al.

It is certified that error appears in the above-identified patent and that said Letters Patent is hereby corrected as shown below:

On the title page item 30

| Patent | Application File |
|---|---|
| Foreign Application Priority Data Section | Replace "Dec. 17, 2009 (GB).......09220666.6" with -- Dec. 17, 2009 (GB)...................0922066.6 -- |

Signed and Sealed this
Sixteenth Day of June, 2015

Michelle K. Lee
*Director of the United States Patent and Trademark Office*